United States Patent [19]

Coats

[11] 4,178,372

[45] Dec. 11, 1979

[54] HYPOALLERGENIC STABILIZED ALOE VERA GEL

[76] Inventor: Billy C. Coats, 1419 Mapleton, Dallas, Tex. 75228

[21] Appl. No.: 883,749

[22] Filed: Mar. 6, 1978

[51] Int. Cl.$^2$ .................. A61K 35/78; A61K 7/26; A61K 47/00

[52] U.S. Cl. .................................. 424/195; 424/58; 424/364

[58] Field of Search ........................................ 424/195

[56] References Cited

U.S. PATENT DOCUMENTS 3,892,853  7/1975  Cobble ................................ 424/195

OTHER PUBLICATIONS

American Perfumer & Aromatics, 1st Documentary Edition Feb. 17, 1960, pp. 124–126 & 130–134.

*Primary Examiner*—Donald B. Moyer
*Attorney, Agent, or Firm*—Richards, Harris & Medlock

[57] ABSTRACT

The clear gel of aloe vera leaves is processed to provide a durable preparation preserving the therapeutic qualities of the fresh gel while essentially eliminating the rare but important idiosyncratic sensitivities encountered from stabilized aloe vera gel of the prior art. The process includes mechanically separating the aloe vera gel matrix from the leaf itself and thereafter adding a catalytic amount of a non-toxic oxidant to the fresh gel which is brought to a temperature of from about 35 degrees C. to about 80 degrees C. Ascorbic acid is then employed as a non-toxic antioxidant to arrest catalytic oxidation and a non-toxic buffer is then added in order to maintain the pH of the stabilized gel composition in a range of from about 4 to about 6. The resulting stabilized aloe vera gel composition closely approaches a nonallergenic status which is a substantial improvement over established aloe vera gels available heretofore, making it especially useful for application to facial areas where such sensitivities are more likely to appear in those few patients who are susceptible. Since treatment of such patients with any effective medication is often problematical, avoidance of interfering sensitivities is of special significance and highly desirable.

15 Claims, No Drawings

HYPOALLERGENIC STABILIZED ALOE VERA GEL

BACKGROUND OF THE INVENTION

Aloe vera, a tropical or subtropical plant of the genus Aloe has lance shaped leaves which contain a viscous but essentially clear gel which is given structural rigidity by hairlike connective fibers that run through it. The clear gel of the aloe vera is to be distinguished from the thick, mucilaginous yellow juice that occurs about the base of the plant leaves and adjacent the rind of the leaf. This juice, known as aloin, has been used for many years as an ingredient in many cathartics and purges.

It is known that the therapeutic qualities of the clear gel of aloe vera leaves depend to a large extent on the freshness of the gel. For example, the pain of a jelly fish sting may be stopped not to recur by applying the clear gel from a leaf that has just been cut, but if the gel has been exposed to air and light for about one and a half hours, these powers are greatly diminished if not lost. In some cases, however, relatively old unstabilized gel has been found to be effective and apparently the varying efficacy of a fresh gel for different medicinal purposes reflects the fact that the gel is a complex mixture of substances whose natural stability on exposure to air and light at different temperatures differ from batch to batch.

In addition to loss of therapeutic efficacy on aging, decomposition products occur after a short time that catalyze further decomposition and make the natural gel even less useful than it might be. For example, the commercially available gel extracts are most difficult to compound into cream bases for topical application because the decomposition products tend to bring about a separation of the cream emulsion. Attempts to use the qualities of the gel in cosmetic preparations have been frustrated since such formulations usually become discolored after about a month, adversely affecting their cosmetic utility. In addition to these difficulties, gel that is over three to four weeks old typically becomes rancid and malodorous. At room temperature (about 70 to 80 degrees F.) it may become rancid within twenty-four hours of cutting.

Many of the problems or preserving the medicinal efficacy of the aloe vera gel and stabilizing it for use in cosmetic compositions can be overcome by following the teachings of U.S. Pat. No. 3,892,853 issued July 1, 1975 to Cobble and assigned to Aloe "99" Inc. That patent, entitled "Stabilized Aloe Vera Gel and Preparation of Same" sets forth a process for stabilizing fresh aloe vera gel which results in a product which can be effectively used for many applications. However, it recently has been determined that a very small percentage of users possess an idiosyncratic sensitivity to a portion of the gel product prepared according to the teachings of that reference. When it does occur, such sensitivity is usually noticed when the gel composition is used as a topical preparation for the face of the patient. It is believed that this difficulty is caused, in part, by the difference in the skin chemistry between facial tissue and other epidermal tissue. Thus, an aloe vera gel composition is needed which is stabile and more nearly nonallergenic (hypoallergenic) when used on facial tissue and other sensitive areas of the skin especially since many such patients have failed to respond to any other mode of therapy.

SUMMARY OF THE INVENTION

The present invention is directed to a method for producing a stabilized, aloe vera gel essentially free from reaction-causing properties. The term "hypoallergenic" as used herein refers to stabilized aloe vera gel compositions which closely approach a nonallergenic, nonirritant status as compared to stabilized aloe vera gels available heretofore. The hypoallergenic aloe vera gel product is produced by mechanically separating the aloe vera gel matrix from the outer cortex of the aloe vera leaf and, after filtering particles of the aloe vera leaf from the gel matrix material, adding a catalytic amount of hydrogen peroxide to the gel and heating the gel to a temperature of from about 35 degrees C. to about 80 degrees C. for a time sufficient to cause the gel to assume a lighter appearance (indicating oxidation). Thereafter, ascorbic acid is added in an amount of from about 0.015 to about 0.05 ounce per gallon of the aloe vera gel composition to thereby arrest catalytic oxidation. Citric acid in the amount of from about 0.4 to about 0.8 ounces per gallon of aloe vera gel is added as necessary to adjust the pH of the composition to within a range of from about 4 to about 6. Other additives, including cetyl alcohol, sorbitol, sodium benzoate, tocopherols and ethyl alcohol are added, as needed, to attain desired cosmetic characteristics. The aloe vera gel prepared in this manner is resistant to degradation upon contact with air and light, retains its medicinal characteristics, and is hypoallergenic when employed as a topical preparation for the face.

DETAILED DESCRIPTION OF THE INVENTION

The raw material for preparing the hypoallergenic stabilized aloe vera gel is obtained from the leaves of fully mature aloe vera plants. Maturity is measured by all active ingredients being present in the leaf in full concentration. A two-year-old plant may be mature but plants which are 4 to 5 years old are preferred to assure full maturity and because they have broader leaves that are easier to handle and contain larger amounts of gel, a factor that lowers percent gel losses when gel is separated from the leaf. In instances where plants are not grown under controlled conditions, the relative proportions of the gel substances is variable, and this causes measuring problems in determining the quantity of reactants needed in stabilizing the gel. To minimize such problems, it is preferred that plants be grown under controlled conditions.

Whatever the relative quality of a plant, best results are obtained, and generally less treatment is required, when the leaves are processed immediately after cutting, the sooner the better. This is because degradative decomposition of the gel material begins on cutting due to natural enzymatic reactions and also due to the activity of bacteria that are normally present on the leaves. After cutting, the leaves are carefully washed in tap water with a suitable detergent, soaked for about five minutes in a suitable nonirritive bactericide and fungicide, such as Microthene, washed with sterilized water, and then dried with a hard finished towel so as not to leave any lint on the plant. Preferably, only the unbruised, nondiscolored portion of the leaves are employed. The gel is then separated from the leaf by cutting off each end of the long leaf and passing it under a roller in order to extrude the gel. The extruded gel falls on a stainless steel tray and is carried to the next purification step in which any large foreign particles, such as pieces of the cortex of the leaf, are separated. This step of the purification process is performed by extruding the gel through a series of apertures sized to retain the above mentioned types of particles. It has been discovered that an extruder which is commercially available and was designed for orange juice processing (for the purpose of removing pulp from the juice) can be used with good results. No homogenization of the unstabilized aloe gel matrix has been found to be necessary in order to produce the hypoallergenic compositions of the present invention.

Once the prepared batch of clear aloe vera gel is extracted from the leaves, a catalytic proportion of hydrogen peroxide is added thereto as a nontoxic oxidant. The stabilization reaction is facilitated by heating the aloe vera gel to a temperature within the range of from about 35 degrees C. to about 80 degrees C. The hydrogen peroxide employed can be added either before the heating step or after, but is preferably added before the gel is heated. While the exact amount of hydrogen peroxide necessary to obtain sufficient catalytic oxidation may vary because of the varying chemical characteristics of the aloe vera gel matrix, normally from about 0.36 to about 0.72 ounce of a 3% aqueous solution of hydrogen peroxide, per gallon of aloe vera gel, has been proven effective. Of course, any other concentration of an aqueous solution of hydrogen peroxide can be employed, the suggested amount of hydrogen peroxide being from about 0.015 to about 0.03 ounce per gallon of aloe vera gel. It should be noted that the indicated quantity of the 3% hydrogen peroxide is about three times that which seems minimally necessary to provide the catalytic oxidation of the gel substances. The excess of hydrogen peroxide is used to accommodate the internal variation in the amount of gel substances which may occur from batch to batch and does not affect the catalytic oxidation of thie step. In general, excess quantities do nothing more than dilute the gel preparation, but if they are added in extreme amounts, they may make the stabilized gel uncomfortable to the skin to which the gel is applied.

The catalytic oxidation resulting from the addition of hydrogen peroxide is allowed to continue for a period sufficient to allow generally complete oxidation of certain of the gel substances, believed to be beta-globulin proteins, and perhaps, alpha-globulin proteins. The heating of the gel substance is continued during the oxidation process and the solution is agitated. Generally the gel will assume a lighter appearance indicating that oxidation is essentially complete. This usually takes no longer than about thirty minutes, but in some instances, positive results have been obtained almost immediately upon adding the oxidant. The time required for oxidation varies with the exact temperatures used and from batch to batch of gel preparations. In general, the change in appearance has most easily and most often been obtained when the oxidant has been added to a preparation that was then held at a temperature of about 49 degrees C. for about ten minutes.

Once the oxidation step has been completed it is necessary to add an antioxidant material in order to arrest the catalytic oxidation. In the past, sorbic acid or the potassium salt of sorbic acid have been used as antioxidants. Use of these materials will result in a stabilized gel composition which is very effective for a wide variety of applications. However, it is believed that the use of these antioxidants in stabilizing the aloe vera gel product could be a contributing factor to sensitivities occasionally reported when aloe vera gels stabilized using those materials were employed as topical facial preparations. Further, when fairly large amounts of ascorbic acid (e.g. 0.23 ounce per gallon) were employed as an antioxidant occasional sensitivities have been reported in certain patients, especially in facial areas. It has been discovered, however, that by employing relatively small amounts of ascorbic acid in combination with citric acid, the necessary antioxidant and buffering effect can be accomplished and that use of these antioxidants, in combination with the other steps of the process of the subject invention, produce a product which is essentially free from this reaction even in proven sensitive persons. In a preferred embodiment of the process of the subject invention, ascorbic acid in an amount from about 0.015 to about 0.05 ounce per gallon of aloe vera gel, (preferably about 0.02 ounce per gallon of aloe vera gel) is first employed in order to arrest the catalytic oxidation of the hydrogen peroxide. Thereafter, citric acid in the amount of about 0.4 to about 0.4 to about 0.8 ounce per gallon of aloe vera gel (preferably in an amount of about 0.5 ounce per gallon of aloe vera gel) is added in order to maintain the pH of the final composition within a range of about 4 to about 6. Preferably sufficient citric acid and ascorbic acid are employed to keep the pH within a range of about 4.4 to about 4.9. In addition to their properties as antioxidants the ascorbic acid and citric acid are important fungicides and bactericides.

Prepared gel treated as described above has been found to possess all known healing qualities of fresh aloe vera gel in full potenty for periods of at least twenty months. However, treated only as described, some substrate substances in the juice of the stabilized gel such as glucose and glucose polymers are subject to bacterial degradation into fermentation products such as ethyl alcohol and acetic acid. This is undesirable if the stabilized gel is to be mixed into a cream base, because the fermentation products cause the cream to separate and also, it gives the preparation an unpleasant odor and appearance. Accordingly, the following additives are utilized to prevent bacterial and/or fungal action on the stabilized gel.

A nontoxic surfactant that will not produce an alkaline pH relative to the amount of buffer present, is added in proportions effective to disrupt and prevent any further coagulation of gel substances such as may have occurred on addition of the catalytic oxidant. Although there have been indications, that the gel substance, or part of it, when dispersed, inhibits or prevents the unwanted bacterial action itself, completely apart from any action of the surfactant, it is preferred to add a nontoxic surface active agent that is bactericidal and/or fungicidal, such as cetyl alcohol. Excellent results have been obtained when cetyl alcohol is employed in an amount of about 0.009 to about 0.027 ounce per gallon of aloe vera gel. Preferably about 0.013 ounce of cetyl alcohol per gallon of aloe vera gel are employed.

In addition to the above indicated surface active additive it may be desirable to employ other additives when the aloe vera gel product is being prepared for use as a topical facial preparation. Thus, for example, 70% sorbitol solution in an amount of about 4.7 to 9.4 ounces per gallon of aloe vera gel can be employed as a moisturizer and mold inhibitor. A preferred amount of 70% sorbitol solution is about 7 ounces per gallon of aloe vera gel. Further, sodium benzoate in an amount of about 0.2 to 0.4 ounce per gallon of aloe vera gel can be employed as an antibacterial useful in facial preparations. A preferred formula employs about 0.24 ounce per gallon of aloe vera gel. Ethyl alcohol in the amount of from about 3.8 to about 5.1 and preferably about 4.5 ounces per gallon of aloe vera gel can be employed for the purpose of preserving the gel, reducing bacterial activity helping to prevent color change of the product, and acting as a long term solubilizing agent for the other stabilizing agents of the preparation.

Although the aloe vera gel treated as disclosed has been found to be stabile and free from decomposition for at least twenty months, certain color changes have been observed in some of these gels during that period. If the gel was heated to 35 degrees C. during the oxidation process, the preparation was likely to assume a neutral beige tint. Heating the gel to 37 degrees C. tended to produce a pink tint in the preparation. Tints of pink, red, and purple, respectively often occurred if the temperature was raised, in the oxidation step of the process, to about 50 degrees C. or higher. The color changes were noted to occur with or without the exposure of a stabilized gel to oxygen. Although such color changes have not affected the therapeutic efficacy of the stabilized preparations, they are deemed undesirable because psychologically a preparation that changes color on the shelf suggests spoilage. Accordingly, a sufficient quantity of tocopherols to inhibit such color change may be added. Vitamin E is one such tocopherol; however, mixtures of alpha, beta, gamma, and delta tocopherols can be employed. Between about 0.0075 and 0.03 ounce per gallon of aloe vera gel can be employed for this purpose. Specifically 0.01 ounce of Vitamin E per gallon of aloe vera gel is preferred.

EXAMPLE

The following example is set forth for the purpose of illustrating one embodiment of the present invention and is not to be interpreted in a limiting fashion.

Mature aloe vera leaves were cut from the plant and the gel extruded therefrom by passing the leaf under a roller. The extruded gel was collected on a stainless steel tray and then forced, under pressure, through an extruder (used commercially to remove pulp from orange juice) to separate particles of aloe vera leaves and foreign substances which may be present in the aloe vera gel matrix. 100 gallons of the aloe vera gel matrix were then heated to approximately 49 degrees C. and 1000 cc's of a 3% hydrogen peroxide solution were added with vigorous stirring until a transient blanching was observed which took about 10 minutes. The gel was then allowed to cool to ambient temperature and ascorbic acid in an amount of 2 ounces was then added to arrest the catalytic oxidation effected by the hydrogen peroxide solution. Subsequently, 50 ounces of citric acid was added to the solution to thereby adjust the pH of the composition to about 4.7. Sorbitol 70% aqueous solution in the amount of 1.5 liters was then added. The water in additive solutions compensates for water loss through evaporation throughout the process. Sodium benzoate in the amount of 24 ounces, vitamin E in the amount of 1 ounce, cetyl alcohol in the amount of 1.28 ounces and ethyl alcohol in the amount of 45 ounces were then added with stirring in order to produce the final composition.

After treatment in this manner the aloe vera gel composition may be concentrated by lyophilization with liquid nitrogen to a predetermined concentrate volume if desired. It may then be transferred to amber bottles and kept in a cool place for future use. Or, as an alternative, it may be stored without such concentration in plastic lined barrels.

The above unconcentrated preparation was prescribed by several dermatologists and used by hundreds of patients suffering from acne problems. The treatment consisted simply of applying the stabilized gel, or a nonoily moisturizing lotion prepared from it, to the face of the patient and excellent results were obtained. The preparation described above also has been employed as an effective nonsteroid anti-inflammatory agent. As pointed out previously, the difference in the facial skin chemistry compared with the skin chemistry of other parts of the body has caused some idiosyncratic sensitivity in a certain few patients treated with stabilized aloe vera gel preparations which have been available in the past. In contrast, the aloe vera gel composition stabilized according to the process set forth above did not precipitate such sensitivities when applied to facial tissue of patients who had proven sensitive to stabilized aloe vera gel preparations of the prior art.

The stabilized aloe vera gel preparations of the subject invention, in addition to its usefulness as a non-oily moisturizer for treating acne, can be effectively employed as a vehicle for antibiotics, steroids, local anesthetics, etc. In this capacity, the ability of stabilized aloe vera gel to penetrate the skin surface and carry other medication with it is especially useful.

While this invention has been described in relation to its preferred embodiments, it is to be understood that various modifications thereof will now be apparent to one skilled in the art upon reading this specification and it is intended to cover all such modifications as fall within the scope of the appended claims.

I claim:

1. A process for stabilizing a clear gel from the leaf of aloe vera comprising:
   (a) mechanically separating aloe vera gel matrix from the outer cortex of aloe vera leaf;
   (b) extruding said gel matrix through a filter to thereby remove particles of aloe vera leaf therefrom;
   (c) heating said aloe vera gel matrix to a temperature within the range of from about 35 degrees C. to about 80 degrees C. and adding thereto a catalytic amount of hydrogen peroxide to thereby cause said gel to oxidize and assume a lighter appearance;
   (d) adding ascorbic acid to said gel in an amount of from about 0.015 to about 0.5 ounce per gallon of said gel to thereby arrest catalytic oxidation;
   (e) adding an amount of citric acid to said gel effective to maintain the pH of said gel solution at a value of between from about 4 to 6.

2. The process of claim 1 wherein said hydrogen peroxide is added in an amount of from about 0.015 to about 0.03 ounce per gallon of aloe vera gel.

3. The process of claim 1 wherein said citric acid is added in an amount of from about 0.4 to about 0.8 ounce per gallon of aloe vera gel.

4. The process of claim 1 and further comprising adding to said stabilized gel composition an aqueous solution of sorbitol.

5. The process of claim 1 further comprising adding from about 0.2 to about 0.4 ounce of sodium benzoate.

6. The process of claim 1 further comprising adding from about 0.009 to about 0.027 ounce of cetyl alcohol per gallon of aloe vera gel.

7. The process of claim 1 further comprising adding from about 3.8 to about 5.1 ounces of ethyl alcohol per gallon of aloe vera gel.

8. The process of claim 1 and further comprising adding an effective proportion of tocopherol to prevent color change in the stabilized gel after processing.

9. The process of claim 8 wherein said tocopherol is vitamin E which is added in an amount of from about 0.0075 to about 0.03 ounce per gallon of aloe vera gel.

10. The process of claim 1 wherein said citric acid is added in an amount effective to maintain the pH of the composition in a range of about 4.6 to about 4.9.

11. The product produced by the process of claim 1.

12. The process for producing a stabilized hypoallergenic aloe vera gel composition comprising:
 (a) mechanically separating the nonbruised and nondiscolored aloe vera gel matrix from the outer green cortex of the aloe vera leaf;
 (b) extruding said aloe vera gel matrix through a filter screen to thereby remove particles of aloe vera leaf therefrom;
 (c) heating said gel to a temperature within the range of from about 35 degrees C. to about 80 degrees C. and adding thereto a sufficient portion of hydrogen peroxide to effect catalytic oxidation;
 (d) allowing said heated gel to cool to ambient temperature and adding thereto ascorbic acid in an amount of from about 0.015 to about 0.5 ounce per gallon of aloe vera gel to thereby arrest said catalytic oxidation;
 (e) adding a sufficient quantity of citric acid to maintain the pH of the composition between from about 4 to about 6;
 (f) thereafter adding from about 4.7 to about 9.4 ounces of a 70% solution of sorbitol, from about 0.2 to about 0.4 ounce sodium benzoate, from about 0.0075 to about 0.03 ounce of vitamin E, from about 0.009 to about 0.027 ounce of cetyl alcohol and from about 3.8 to about 5.1 ounces of ethyl alcohol, said additions being made per gallon of aloe vera gel.

13. The process of claim 12 wherein said hydrogen peroxide is added in an amount of from about 0.015 to about 0.03 ounce per gallon of aloe vera gel.

14. The process of claim 12 wherein sufficient citric acid is added to maintain the pH of the composition between about 4.4 to about 4.9.

15. In a process for stabilizing a clear gel from the leaf of the aloe vera, which includes the steps of mechanically separating the aloe vera gel matrix from the outer cortex of the aloe vera leaf, filtering particles of the aloe vera leaf from the gel matrix, heating the aloe vera gel matrix to temperatures of from about 35 degrees to about 80 degrees and adding a catalytic amount of hydrogen peroxide to cause the gel to oxidize and assume a lighter appearance, the improvement comprising:
 adding ascorbic acid to said gel in an amount of from about 0.015 to about 0.5 ounce per gallon of said gel to thereby arrest catalytic oxidation and adding an amount of citric acid to said gel which is effective to maintain the pH of the gel at a value of between from about 4 to about 6.

* * * * *

UNITED STATES PATENT AND TRADEMARK OFFICE
CERTIFICATE OF CORRECTION

PATENT NO. : 4,178,372
DATED : December 11, 1979
INVENTOR(S) : Billy C. Coats

It is certified that error appears in the above–identified patent and that said Letters Patent are hereby corrected as shown below:

Column 1, line 46, change "or" to --of--.
Column 3, line 38, change "thie" to --this--.
Column 4, line 21, change "0.4 to about 0.4 to" to --0.4 to--.
Column 6, line 15, change "has" to --had--.
         line 54 (Claim 1), change "4 to 6" to --4 to about 6--.

Signed and Sealed this

Fifteenth Day of April 1980

[SEAL]

Attest:

SIDNEY A. DIAMOND

Attesting Officer      Commissioner of Patents and Trademarks